United States Patent [19]

Wohlwend

[11] Patent Number: 5,493,865

[45] Date of Patent: Feb. 27, 1996

[54] METHOD AND APPARATUS FOR VITRIFICATION OF WATER OR MOISTURE-CONTAINING TEST SAMPLES, PARTICULARLY BIOLOGICAL SAMPLES

[76] Inventor: Martin Wohlwend, Bifig, CH-9466 Sennwald, Switzerland

[21] Appl. No.: 285,110

[22] Filed: Aug. 3, 1994

[30] Foreign Application Priority Data

Aug. 3, 1993 [CH] Switzerland .............. 02 321/93

[51] Int. Cl.$^6$ .................................................. F25B 19/00
[52] U.S. Cl. .................................................. 62/51.1; 62/78
[58] Field of Search .................................. 62/64, 78, 51.1

[56] References Cited

U.S. PATENT DOCUMENTS

| | | | |
|---|---|---|---|
| 4,559,298 | 12/1985 | Fahy | 62/78 |
| 4,685,305 | 8/1987 | Burg | 62/78 |
| 4,688,387 | 8/1987 | Conaway | 62/78 |
| 4,753,887 | 6/1988 | Bellare et al. | 435/287 |
| 4,799,361 | 1/1989 | Linner | 62/64 |

FOREIGN PATENT DOCUMENTS 1806741  6/1969  Germany .

OTHER PUBLICATIONS

Publication by BALZERS Union AG of Balzers, Principality of Liechtenstein: "Elektronenmikroskopie—Hochdruck–Gefriermaschine HPM 010" ( Electron Microscopy—High-Pressure Freezing Machine HPM 010).
Studer et al, High Pressure Freezing comes of Age, Scanning Microscopy, Supplement 3, 1989, pp. 253–269.
Kanno et al. (1975), "Supercooling of water to −92° C. under pressure". Science 189:880–881.
Moor H. (1987), Theory and practice of high pressure freezing. In: Steinbrecht R. A. Zierold K (eds) Cryotechniques in Biological Electron Microscopy, Berlin, Springer, 175–191.
Michel et al. (1991), J. Microsc. 163:3–18.

*Primary Examiner*—Ronald C. Capossela
*Attorney, Agent, or Firm*—Frishauf, Holtz, Goodman, Langer & Chick

[57] ABSTRACT

To vitrify a sample, for example a biological sample which has a high water content, without the formation of ice crystals, the sample (10) is placed in a closed test chamber (11) having a chamber outlet (35). The chamber (11), with the sample therein, is filled with a primary fluid without cooling the sample to freezing temperature. This primary fluid may be an alcohol. The sample is vitrified by applying a high-pressure cryogenic fluid against the sample at a substantial pressure. The step of maintaining the pressure is accomplished, in accordance with the invention, by maintaining the outlet (35) from the chamber (11) at least essentially closed by a closing element, typically a valve (41), until the pressure within the sample chamber (11) has reached a predetermined value. The primary fluid may be a portion of the cryogenic fluid itself, for example heated, or even cooled, to an appropriate temperature which, however, will not cause the sample to freeze. Automatic interlocks (63; 32) can be provided to ensure that the high-pressure cryogenic fluid is applied only after the chamber has been filled and pressurized by the primary fluid. A pressure rise to 2,100 bar, and more, in 20 milliseconds can be obtaining, resulting in a high cooling rate of at least 20,000° C. per second, which cools the sample. Liquid nitrogen is a suitable cryogenic fluid.

24 Claims, 3 Drawing Sheets

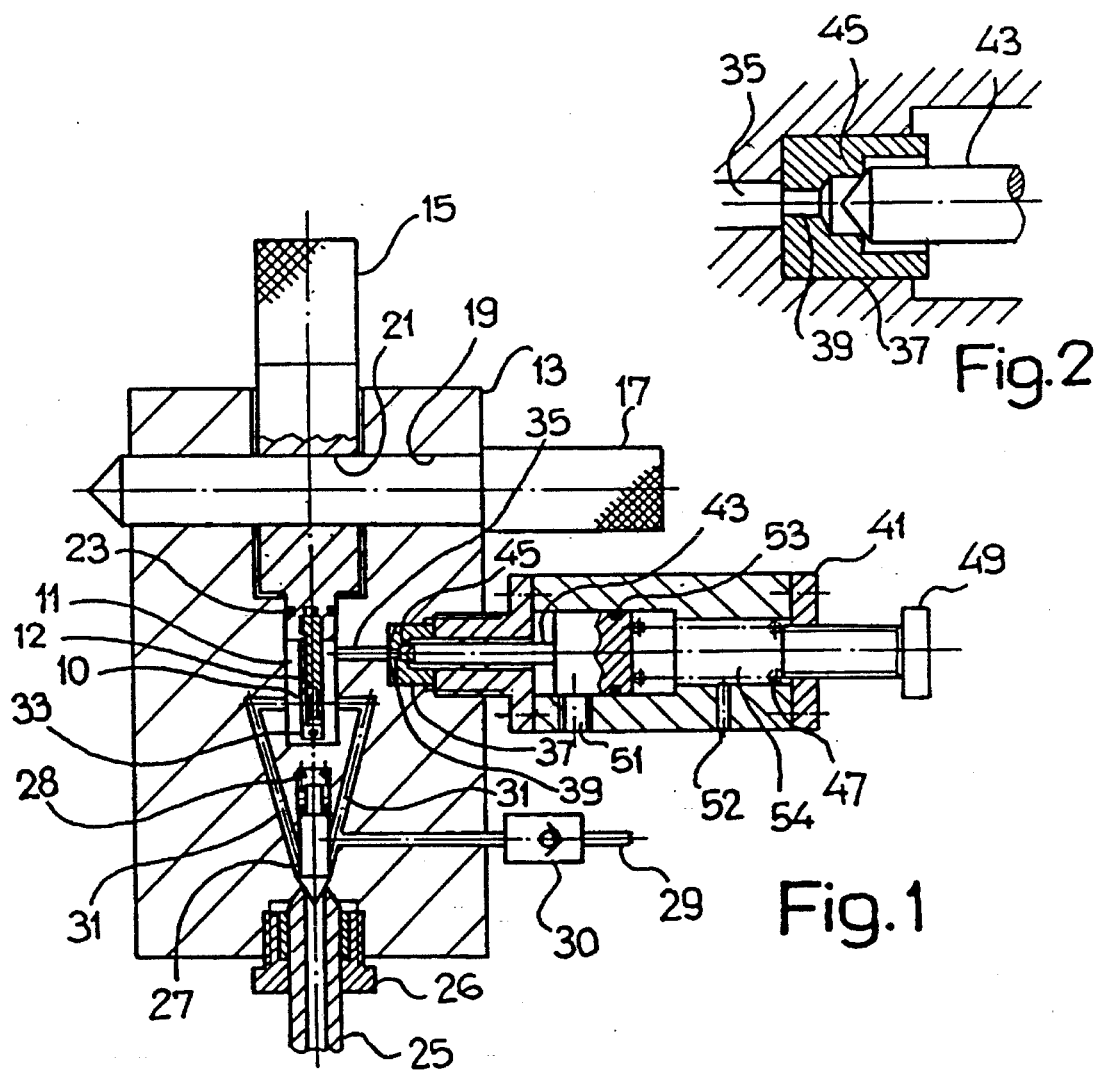
Fig. 2
Fig. 1
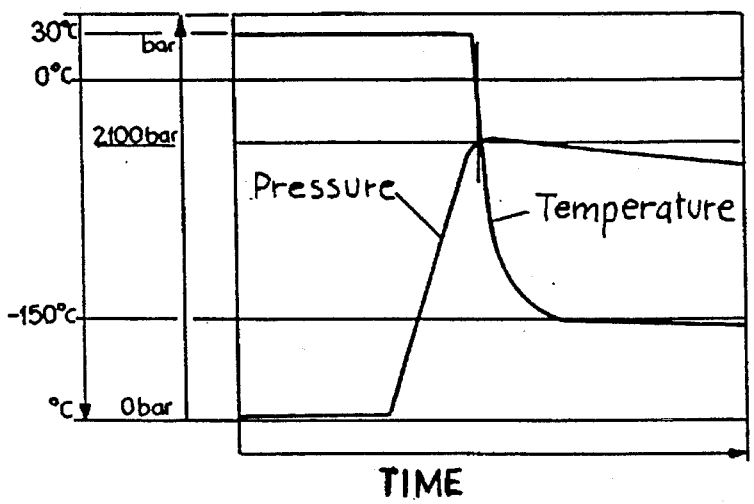
Fig. 3

METHOD AND APPARATUS FOR VITRIFICATION OF WATER OR MOISTURE-CONTAINING TEST SAMPLES, PARTICULARLY BIOLOGICAL SAMPLES

FIELD OF THE INVENTION

The present invention relates to preparation of test samples which contain fluids such as water, subject to freezing, and in which the fluid is frozen at such a rate that it vitrifies, rather than form crystals or otherwise interferes with the integrity of the test sample for subsequent imaging in a transmission electron microscope (TEM).

BACKGROUND, and Historical Review of Preparation of Samples for Transmission Electron Microscopy.

To permit description of biological structures with high resolution, that is, 1–3 nm, it is customary to use a transmission electron microscope (TEM) to image the structure. The high vacuum which forms the environment for the sample in the TEM, in the order of $10^{-6}$ mbar, as well as the capability of penetrating extremely thin slivers of samples, for example 0.1 μm thick, requires preparation methods for the biological test samples which do not interfere with the structure of the samples and, further, permit the samples to withstand the thin slicing as well as the vacuum.

It has been proposed to chemically fix the biological test samples for TEM use. In a first step, the samples are cross-linked in a suitable buffer solution, then dewatered or dessicated with a suitable solvent. The sample is then penetrated with monomers and polymerized. Such samples can then be sliced very thinly and examined in the TEM. It has been known for decades, however, that this chemical process affects the samples. Entire cells or portions of cells may shrink or blow or expand. Molecules are not fixed in situ, but may shift. Diffusible ions are not immobilized.

The only alternative to chemical fixation of test samples is by freezing. In this method, a first solidification step solidifies the biological sample by rapid cooling. The methods which permit investigation by a TEM are substituted by freezing with subsequent embedding, frozen etching and cutting or severing while frozen. The test samples are well immobilized by freezing and have a microstructure which is quite similar to the actual structure which the test sample has. Thus, the freezing fixation is superior to chemical fixation—see Studer et al, High Pressure Freezing comes of Age, Scanning Microscopy Supplement 3, 1989, pp. 253–269.

Biological samples have a moisture or water content of between 30–95%. Upon immobilizing by freezing, two different events may occur, in dependence on whether the freezing step is rapid or slow.

If the freezing is slow, herein considered to be several hundred degrees C. per second, ice will form and a massive phase separation will occur within the biological sample. Growing ice crystals which only consist of water molecules concentrate at their edges the materials contained within the cellular fluid, such as sugar, proteins, nucleic acids, fats, ions and the like. Test samples immobilized by freezing in this matter have segregation patterns, that is, network patterns which are very fine, within the nanometer region, or even rather coarse, that is, within the micrometer region. Such test samples do not form suitable alternatives to chemically fixed samples.

If cooling is rapid, that is at a rate of more than a million degrees C. per second, it is possible to vitrify the biological sample. At such freezing rate, there is no time for water molecules to form ice crystals. Rather, they become stiff or solidify and form a solid amorphous body. The vitrified state of water is stable below −135° C. Vitrified samples maintain the desired structure which is representative of the actual structural condition, see Michel et al. (1991), J. Microsc. 163:3–18.

To obtain vitrification, it is necessary to have very high cooling rates, that is, the temperature of the sample, with respect to time, must drop rapidly. Such cooling rates can be obtained at the surface of a sample by all customary freezing methods which operate under atmospheric pressure. Within the interior of the sample, however, the cooling rate depends entirely on the physical characteristics of the object. For pure water, the maximum cooling rate in the center of a layer of 0.1 mm thickness, which is optimally cooled from both sides, is about 14,000° C. per second, for a temperature drop between 0° C. and −90° C. This means that it is possible to vitrify only very thin samples. Results actually obtained in practice show that the test samples are frozen without interfering ice formation by only a few micrometers removed from the surface. In order to be able to vitrify thicker biological test samples, it is necessary to change the freezing characteristics of the samples. It has been proposed to add antifreeze substances, or to use high hydrostatic pressure.

Adding antifreeze substances permits vitrification with low freezing rates. However, it is necessary to first chemically cross-link biological test samples before they can be treated with antifreeze materials. The result is that the maintenance of the structure of the test sample is no better than in chemical fixation. Use of antifreeze materials, thus, is no further considered when an improved imaging of the structure, with ultra-precision is desired.

Using hydrostatic pressure which is high, in the order of 2,045 bar, lowers the melting point of water which, as well known, is 0° C. at atmospheric pressure, to about −22° C. Supercooling, which at atmospheric pressure is −39° C., can be dropped, by pressure, to −92° C., see Kanno et al. (1975), "Supercooling of water to −92° C. under pressure". Science 189:880–881. It has been believed, based on theoretical considerations, that biological samples could be vitrified at a pressure of 2,045 bar at a cooling rate of several 100° C. per second, see Moor H. (1987), Theory and practice of high pressure freezing. In: Steinbrecht R. A., Zierold K (eds) Cryotechniques in Biological Electron Microscopy, Berlin, Springer, 175–191.

Moor and his collaborators developed a high-pressure freezing machine in which liquid nitrogen at a temperature of −150° C. is impinged on the biological sample. The samples are held in a sample carrier by two disk-like gold plates. The gold plates have a diameter of 3 mm, and a thickness of 0.6 mm, and are formed with a recess of 0.5 mm. The recess diameter is 2 mm. This prevents destruction of the probes during the rise in pressure and the cooling step.

High-pressure freezing machines are described in the referenced German Patent 1 806 741, Moor et al., and the Publication by BALZERS Union AG of Balzers, Principality of Liechenstein: "Elektronenmikroskopie—Hochdruck-Gefriermaschine HPM 010" ("Electron Microscopy—High-Pressure Freezing Machine HPM 010"). A commercially available machine provides a guarantee of a pressure rise to 2,000 bar in about 25 milliseconds. The sample is cooled immediately after reaching the 2,000 bar pressure at a cooling rate of 5,000° C./sec (Moor, 1987, referred to above). The coordination of pressure rise and cooling of the sample is obtained by filling the test sample chamber with alcohol before the freezing step. Upon introduction of liquid nitrogen, the pressure rises rapidly, and the alcohol first and then the nitrogen can vent through an opening in the test chamber. Practical results have shown that there are biological samples which can be vitrified up to a thickness of about 0.150 mm. Test samples were early or young leaves of apple trees (Michel et al., 1991, supra). One can deduce therefrom that the freezing characteristics of apple tree leaves are relatively good, that is, freezing rates of several thousand ° C./sec., and under a pressure of 2,045 bar, are sufficient in order to obtain vitrification. Other biological samples, however, and particularly animal tissue, could not be immobilized just as well by cold. Cartilage tissue, for example, which is 80% water, is vitrified under these conditions only at the surface. The samples were 0.2 mm thick, and the vitrification depth was only about 0.02 mm. One can deduce therefrom that the physical characteristics of biological samples define the limits of possibility of vitrification. There is a need to obtain ideal cooling conditions.

The commercial high-pressure freezing machine reaches values which are not optimal for all uses and cannot be improved by simple modification. The commercial machine has a pressure rise of about 25 milliseconds and a freezing rate of 5,000° C./sec. between 0° C. and −50° C. If the pressure period is increased by increasing the outlet from the test sample chamber, a higher throughput rate of liquid nitrogen can be obtained and a higher cooling rate will result. Such change, however, so interferes with the coordination of pressure rise and temperature drop that the biological test sample is cooled before the 2,000 bar pressure is obtained. Consequently, the sample is frozen while forming ice crystals and will not vitrify, although the cooling rate is high.

THE INVENTION

It is an object to provide a method and an apparatus which ensures that the necessary parameters, namely pressure rise, temperature drop and cooling rate, are always properly coordinated, and wherein the cooling rate is as high as possible.

Briefly, the test samples are introduced into a chamber which is filled with a primary fluid, but does not cool the sample to freezing temperature. In order to vitrify the sample, the test sample is subjected to a cryogenic fluid under high pressure. This cryogenic fluid ejects the primary fluid from the test chamber through an opening in the chamber holding the test sample.

In accordance with a feature of the invention, the outlet opening from the fluid chamber is a duct which is first maintained essentially closed until the pressure within the chamber has reached a predetermined value. This permits ejection of the primary fluid into the duct by the cryogenic high-pressure fluid, and results in an extremely rapid pressure rise with simultaneous rapid cooling. The pressure may rise, for example, to 2,100 bar in 20 milliseconds, simultaneously supercooling the sample. This minimizes any possible damages which might result due to the pressure on the biological sample. The method, further, guarantees a high cooling rate of 20,000° C./sec., and more.

Optimal cooling of the test sample means that the freezing characteristics of the samples themselves define the thickness of the vitrified layer. The high cooling rate can be obtained by dimensioning the opening in the test chamber to be relatively large, so that, due to a high throughput flow rate, the sample is cooled extremely rapidly. For example, it was possible to completely vitrify cartilage disks of 0.150 mm thickness; previously, vitrification was possible only to a depth of 0.020 mm.

The primary fluid to fill the test chamber can be of various types. For example, as customary, a fluid can be used, the freezing point temperature of which is above the freezing point of the test sample. It is also possible to use a fluid which has a temperature below the freezing point of the test sample, if the filling is carried out rapidly and the cryogenic fluid then is immediately injected so that the sample is not cooled by the primary fluid below the freezing point of the sample before the requisite pressure has reached the supercooling value appropriate for the sample. This arrangement makes it possible to use cryogenic fluid also as the primary fluid and to vitrify the sample by subsequent admission of the same cryogenic fluid under high pressure. It may be desirable to heat the portion of the cryogenic fluid forming the primary fluid, which is used to first fill the chamber; or, alternatively, to cool the cryogenic fluid used as primary fluid, so that the test sample is maintained at the appropriate temperature during filling and is not undesirably cooled or heated.

Liquid nitrogen is suitable as a cryogenic fluid, under a pressure of at least 2,100 bar, and preferably higher.

The primary fluid to fill the test chamber can be a fluid which usually is at a temperature which is higher than the freezing point of the sample. Upon repeated operation, the housing structure will cool and the primary fluid might freeze before it reaches the sample. Under some conditions, it is desirable that the liquid freezes only at relatively low temperature. A suitable liquid is, for example, isopropanol, which has a freezing point of −88.5° C.

In accordance with another feature of the invention, the apparatus to carry out the method has a test chamber with a fluid outlet duct, essentially closeable by an outlet closing or throttling element to permit sufficient back-pressure to build up in the sample chamber. A controllable pressure valve is suitable. This closing or throttling element prevents venting of the primary fluid from the test sample until the pressure within the chamber has reached a predetermined value.

The closing element, preferably, is a spring-loaded valve which permits simple construction. The pre-setting or pre-stressing of the spring can be easily controlled, for example by a screw. This readily permits control of the pressure under which the valve opens. Alternatively, a controllable throttle, e.g. a slightly open throttling valve, may be used.

In accordance with a preferred feature of the invention, a valve is provided in advance of the inlet to the test chamber which opens only when a high, predetermined pressure is applied thereto, so that the pressure build-up of the primary fluid within the chamber can occur as rapidly as possible. A valve positioned as close to the test sample chamber as possible can ensure that when the appropriate pressure has been reached, or some other predetermined pressure has been reached, supply of the primary fluid is terminated in order to then directly supply the cryogenic fluid to the test chamber. The closing element and the structure which disconnects supply of the primary fluid and the supply of the cryogenic fluid to the chamber are, preferably, coupled together. After operation of the closing element, then, necessarily cryogenic fluid will be supplied to the test chamber. As mentioned above, cryogenic fluid can be used to fill the test chamber, that is, to also form the primary fluid. In its simplest form, a bypass can be provided which leads from a source of cryogenic fluid to the test chamber. This has the advantage that the use of isopropanol can be avoided. Since this material is customarily vented, no environmentally undesirable alcohol vapors will be vented in the atmosphere. Preferably, the bypass includes a heat exchanger for heating and/or cooling of the cryogenic fluid utilized as a primary fluid, in order to ensure that the sample is not unduly cooled, or heated, while in the test chamber.

Preferably, the closing element, in form of a valve, is so constructed that the valve nozzle can be exchanged. This permits use of valves which have a smaller or larger valve pass diameter, or nozzle opening, or valve seat diameter. The cooling rate can thus be easily adjusted by suitable choice of the diameter of the nozzle, or valve seat, or valve throughput opening, and the valve setting, respectively.

DRAWINGS

FIG. 1 is a highly schematic vertical cross-sectional view through an apparatus in accordance with the present invention;

FIG. 2 is a fragmentary cross-sectional view, to a highly enlarged scale, of the closing nozzle and valve, as well as the valve element used in the apparatus of FIG. 1;

FIG. 3 is a diagram illustrating the course of pressure and temperature, with respect to time (on the abscissa);

DETAILED DESCRIPTION

Figure 4:
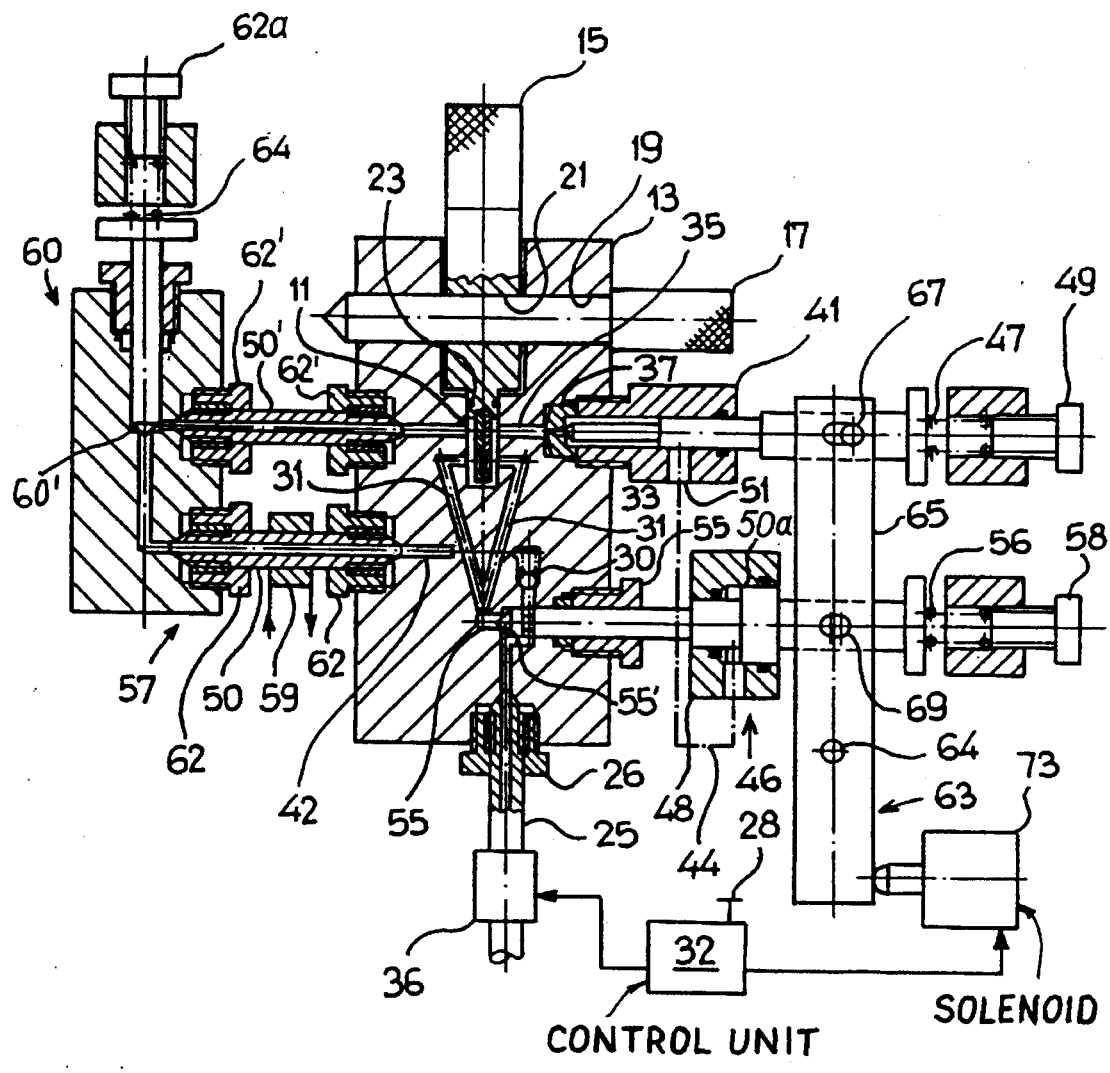
FIG. 4 is a vertical cross-sectional view of another embodiment of the invention, in which the cryogenic fluid can be used as a primary fluid.

Referring first to FIG. 1: A block 13 is hollowed to form a test sample chamber 11. The chamber 11 is closed by a closing element or cover 15. A bolt 17, passing through an opening in the closing element 15 ensures safe seating of the cover 15 and closing of the chamber 11. The bolt 17 passes through a bore 19 in block 13 and the bore 21 in the cover 15. An O-ring 23 seals the cover 15. A high-pressure connection 25 for cryogenic fluid is located at the lower part of block 13, secured in position by a nut 26. The cryogenic fluid, for example liquid nitrogen, has a pressure of at least 2,100 bar, preferably about 2,500 bar. A check valve 27 with a spring 28 prevents back-flow of the cryogenic fluid.

A connection line 29, with an interposed check valve 30, is connected to the chamber 11 to permit initial filling of the chamber 11 with a primary fluid before the liquid nitrogen is applied to the test chamber 11. The primary fluid which is supplied has a freezing point which is above that of the test sample 10. The check valve 30 prevents back-flow of the primary fluid. The ducts 31 are used to supply both the primary fluid as well as, later on, the cryogenic fluid to the test chamber 11.

The test sample 10 is held in a holder formed by two disk-like plates 12 formed with a recess. They are held in position in the chamber 11 by a sample holder 33. The space in the recesses which is not filled by the test sample should be filled by a liquid, for example 1-hexadecene since, if any air would be left in the space, the effect of the high pressure would be weakened, and the cooling rate decreased.

The chamber 11 has an outlet portion 35, formed by a duct in the block 13.

In accordance with a feature of the invention, and to ensure appropriate back-pressure in chamber 11 during cooling, the outlet portion 35 is blocked by a closing element 41, formed by a valve. This valve has a replaceable nozzle 37, coupled to the outlet 35 (see FIG. 2), to permit the nozzle 37 to be readily exchanged for nozzle elements with larger or smaller nozzle openings 39. If the diameter of the valve seat 45 is always maintained the same, the valve 41 will always open at the same pressure.

The valve 41 has a valve body 43 which is operatively associated with the valve seat 45, formed on the nozzle 37. A spring 47 generates the closing force for the valve. The spring pressure can be controlled or adjusted by an adjustment screw 49. An O-ring 53 seals the spring chamber 54 within which the spring 47 is retained. The valve 41 has a vent opening 51, leading to ambient space. The spring chamber 54 is vented by a bore 52.

Operation

To vitrify a test sample, the bolt 17 is removed, the cover element 15 removed from the block 13, and the sample 10 inserted in the sample holder 33. The sample holder can be secured to the cover element 15. The cover element, after insertion, is secured by the bolt 17.

The first step in the freezing operation is to introduce the primary fluid, for example isopropyl alcohol, through the line 29 and the check valve 30 into the test chamber 11. The temperature of isopropyl alcohol should be above the freezing point of the test sample.

In a next step, cryogenic fluid, for example liquid nitrogen, is introduced through the stub 25 and check valve 27 into the test chamber 11. Since the test chamber is closed, the pressure will rise rapidly. As soon as the pressure has reached the opening pressure setting of the valve 41, the primary fluid will be drained rapidly from the chamber and, consequently, a fresh flow of cryogenic fluid will follow. This results in a maximum cooling rate, see the diagram of FIG. 3.

It is possible to so select the diameter of the valve flow passage 39 such that the desired pressure will be maintained for the period of time necessary for vitrification of the test sample. When the valve 41 opens, the valve body 43 is moved to the right (FIG. 1), and the primary fluid can escape through the exhaust or drain 51.

In the example described, the chamber 11 was filled with an alcohol. The embodiment of FIG. 4 permits vitrification without a primary fluid which differs from the cryogenic fluid.

Referring now to FIG. 4, which illustrates, in general, a test apparatus similar to that of FIG. 1; identical parts have been given the same reference numerals. Similar parts have been the same reference numerals with prime notation.

In the embodiment of FIG. 4, the same fluid is used as a primary fluid for introduction into the test chamber, to build up pressure, and to vitrify. Thus, the connection line 29 of FIG. 1 is not needed. A valve 55 is provided, however, in which liquid nitrogen can be conducted either into a bypass 57 and then into the test chamber or, respectively, directly into the test chamber 11. Each one of these fluid paths will, however, provide fluid of different temperature into the test chamber. In the description which follows, two different fluids will be referred to. The nature of the fluid is the same, their temperature, however, differs.

Valve 55 is maintained by the spring 56. In the position shown in FIG. 4, permitting fluid from inlet 25 to flow through the bypass 57. Adjustment screw 58 permits presetting of the tension of the spring 56. The adjustment could be such that the valve needle or a slider 55' is shifted already before the opening of the valve 41 counter the force of the spring 56, so that the bypass is turned OFF or disconnected or blocked, and cryogenic fluid can flow through the duct 31 to the test chamber 11. Since the surface of the valve needle or slider 55' now has pressure applied thereto, the valve slider remains in the switched-over position.

The bypass 57, essentially, has a line 42 and two screw fittings 62, 62' to the block 13 as well as coupling elements 50, 50'.

The function of the bypass 57 is to control the temperature of that portion of the cryogenic fluid which is first applied to the test chamber 11 to form the primary fluid. This temperature control of the portion of the cryogenic fluid should be such that, during the short period of time which is required in order to fill the chamber 11, it is not capable of cooling the test sample 10 in the chamber 11 to freezing temperature. This temperature control can be achieved in various ways, for example by a heat exchanger 59 which can cool or heat the fluid supplied thereto. The check valve 30 is located within the bypass 57 in order to prevent backflow of the primary fluid. The valve 60, also located within the bypass element 57, is an overpressure valve which opens only when a predetermined pressure is reached, for example 1,300 to 2,500 bar, and then remains open, in order to permit fluid to fill the test chamber 11. The valve 60 remains open because the comparatively large surface at the end face of the movable valve element 60' is subject to pressure. The over-pressure valve 60 is further controlled by a set screw 62a which controls the bias setting of the spring 64. The valve 60, preferably, opens only at a pressure of about 2,100 bar, so that pressure rise in the test chamber 11 occurs within a few milliseconds.

As in the embodiment of FIG. 1, the valve 41 is provided in form of an over-pressure valve which blocks the chamber outlet 35 until the pressure within the chamber 11 has reached a predetermined value.

The system is provided with an interlock which is ensures that at the latest when the valve 41 opens, valve 55 switches over in order to block supply of the primary fluid, that is, the temperature-controlled fluid, via the bypass 57 and, in turn, directly connect the cryogenic fluid from inlet 25 via the short ducts 31 into the chamber 11. These interlock elements can be formed, for example, by a coupling arrangement 63. This coupling arrangement, simultaneously, can also ensure that after vitrification, pressure in the apparatus is decreased.

The interlock coupling system includes a pin 64 about which a lever 65 is rotatable. A connector dog 67, secured to the valve stem of valve 57, and a carry-along dog 69 secured to the valve 55, are each coupled to the lever 65. When the valve 41 opens, the carry-on dog 67 rotates lever 65 in clockwise direction (with respect to FIG. 4). This causes the lever 65 to carry along the dog 69 of valve 55, which switches over the valve 55 so that the fluid applied through line 25 will flow through the ducts 31 into the test chamber 11.

Alternatively, it would also be possible to operate the valve 55 pneumatically, for example by coupling to the exhaust line 55 of the valve 41. The pneumatic alternative, which may be added as an additional safety feature together with the mechanical system, is shown, schematically, by the chain-dotted line 44, which illustrates, diagrammatically, that at least a portion of the fluid emitted from the drain 51 operates a cylinder 46, formed by the cylinder housing 48 and piston 50a. Alternatively, the valve 55 could be a magnetic valve which switches over under electrical control based on a control signal which responds to opening of the valve 41.

Operation, embodiment of FIG. 4

The chamber 11 is loaded with the sample 10, as described in connection with FIG. 1. Upon operating a start button 28 of a control unit 32, the control unit operates valve 36 which supplies cryogenic fluid, for example liquid nitrogen, at a pressure of about 2,100 bar or more. This cryogenic fluid flows over valve 55 into the bypass unit 57. At a predetermined pressure, for example 2,100 bar, valve 60 will open. The heat exchanger unit 59, forming a heating/cooling apparatus, thermostatically controls the temperature of the fluid which will flow through line 50' and connections 62, 62' into the chamber 11. The chamber is filled within a few milliseconds. This, deliberately, eliminates the customary fill of the test chamber 11 with an alcohol.

The pressure will rise rapidly, and the valve 41 will open. Filling of the chamber 11, and pressure rise, occurs so rapidly that the suitably temperature-controlled fluid is not capable of freezing the sample. Since the outlet valve 41 is coupled to the switch-over valve 55, valve 55 will reliably switch over and permit the pressurized cryogenic fluid to be directly supplied to the test chamber 11. Switch-over of the valve 55 can be readily controlled by suitable adjustment of the spring 56 which, preferably, is so set that valve 55 will switch over shortly before the pressure has risen to its final value by shifting the pressure acting on the face or valve needle end 55' counter the force of the spring 56, to shift the valve 55.

After switch-over of the valve 55, cryogenic fluid is supplied directly to the chamber 11 under high pressure, resulting in extremely rapid cooling of the sample under high pressure. Measured cooling rates of from 0° to −100° C. within 10 milliseconds correspond to a rate of 20,000° C. per second, and thus are a substantial multiple higher than those previously obtained by prior art apparatus.

After vitrification is complete, the control apparatus 32 closes the valve 36, and interrupts supply of cryogenic fluid into the apparatus. At the same time, the control system 32 controls a solenoid 73 which engages the lever 65 in order to retain the valve 41 in open position and the valve 55 in the switched-over position until the pressure in the entire system has totally dissipated.

Figure 5:
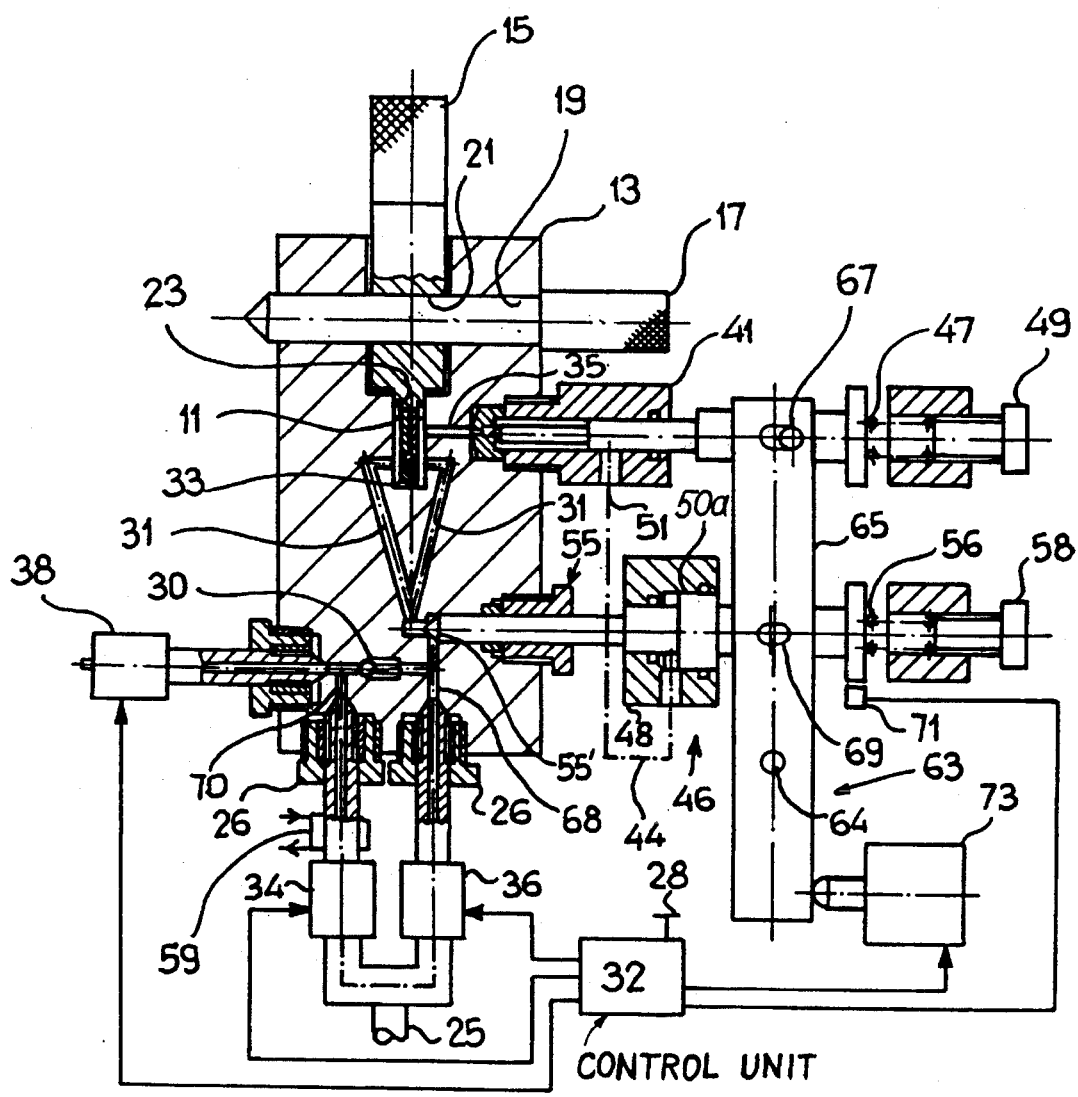
FIG. 5 is a vertical cross-sectional view, in highly schematic representation, of another embodiment of the invention.

Embodiment of FIG. 5

This embodiment, which is preferred, is a simplification of the apparatus of FIG. 4 and, as in FIG. 4, permits vitrification without alcohol.

As best seen in FIG. 5, valve 55 is used to first supply a temperature-controlled fluid to fill the chamber 11 and build up pressure therein, and then supply the cryogenic fluid for vitrification of the sample within the chamber 11. The valve 55 switches over when the pressure has reached a predetermined value. The primary fluid, of course, can again be the cryogenic fluid, suitably temperature-controlled for the pre-pressurization function.

Supply of the fluids to the chamber 11 is effected directly via the ducts 31. As in the embodiment of FIG. 4, the fluid to fill the chamber 11 and build up the pressure as well as the fluid for vitrification are the same; usually, however, the temperatures of the two fluid streams will be different, in accordance with the requirements of the nature of the samples to be vitrified.

Differing from the apparatus of FIG. 4, the supply line 25 is split and leads additionally to the valve 34, to which, downstream, the heat exchanger 59 forming a heating/cooling system is connected. The bypass line 70 then is conducted over the check valve 30 to the valve 51. Valve 55 is equipped with a sensor 71 which responds upon switch-over of valve 55 and provides a signal to the control unit 32 so that the control unit 32 can cause closing of the valve 34 and opening of the valve 36.

Operation of embodiment of FIG. 5

Upon commanding the control unit 32 to start, for example by depression of key 28, valve 34 will open, and a portion of cryogenic fluid from line 25 will flow into bypass line 70, temperature-controlled by the heat exchanger 59. The temperature of the sample, thus, will not change essentially during the build-up of pressure. As soon as the pressure set by valve 55, for example 1,600 bar, has been reached, valve 55 will open and, based on the larger surface of the end face of the valve needle or slider 55', is maintained in open position. The temperature-controlled fluid, that is, the primary fluid, will flow through the ducts 31 into the chamber 11 to fill chamber 11. Since the fluid has a pressure of at least 2,100 bar, and usually higher, or, some other predetermined pressure in dependence on the nature of the sample, fill within the test chamber 11 and rise to the required pressure will occur within a few milliseconds. Simultaneously with opening of the valve 55, valve 34 closes, and valve 36 will be opened; with slight delay, valve 38 coupled to the bypass 70, will also open, in order to vent the bypass 70. Cryogenic fluid will now be supplied directly over the ducts 31 to the chamber 11.

As soon as the predetermined pressure is reached in the chamber 11, filled with temperature-controlled fluid, the valve 41 will open, the temperature-controlled fluid is ejected into and through the fluid outlet opening 35, and cryogenic fluid can flow into the chamber 11 to vitrify the sample. After vitrification, valve 36 closes. The solenoid 73 operates to hold the valve 41 in open position and the valve 55 in the shifted position until the pressure in the entire system is completely dissipated. Thereafter, valves 34 and 38 can again be closed, and the apparatus is ready to receive another sample.

Various changes and modifications may be made, and any features described herein may be used with any of the others, within the scope of the inventive concept.

For example, in the embodiment of FIG. 5, bypass 70 could be omitted if the volume of the test chamber 11 and of the fluid outlet duct 35 is so small that the pressure rise can be obtained within a few milliseconds.

It is not necessary that the fluid outlet opening be completely closed while the pressure rises during filling with primary fluid. A high degree of throttling, which results in substantial back-pressure, could also be used for example by a leaky valve or a throttle which also, selectively, allows unthrottled throughput, similar to an open valve, referred to, generically, as a "controllable throttling or closing element". Consequently, in the specification and claims as used herein "closed" should be considered as "essentially closed" in other words, sufficiently closed or throttled, to obtain the feature of the invention illustrated best in FIG. 3, namely that the high pressure is obtained at about the time that the sample is sufficiently cooled, so that the coordination of pressure rise and temperature drop is such that the biological sample will be under high pressure at the time or before it is substantially cooled to prevent the formation of ice crystals, which would obtain if the high pressure is delayed or does not become available until after freezing has started. Thus, the element 41, which has been described as a closing element, can also be considered to be a leaky closing or highly throttling element, permitting the build-up of pressure in the chamber simultaneously with super-cooling the test sample.

I claim:

1. A method for vitrification of samples (10), including biological samples, particularly biological samples, comprising the steps of introducing the sample (10) into a closed test sample chamber (11) having a chamber outlet (35);

filling the chamber (11), with the sample (10) therein, with a primary fluid without cooling the sample to freezing temperature; and further comprising, the step of establishing pressure for cooling and vitrifying the sample by introducing a highly pressurized cryogenic fluid into the test sample chamber (11) while inhibiting unrestricted escape of the highly pressurized cryogenic fluid from the test sample chamber to establish pressure therein, and cooling the sample in the test chamber (11) to vitrification temperature.

2. The method of claim 1, wherein said step of inhibiting unrestricted escape of the highly pressurized cryogenic fluid comprises maintaining the outlet (35) from the test chamber (11) essentially closed by a throttling or closing element (41) until the pressure supplied by the pressurized cryogenic fluid within the test chamber (11) has reached a predetermined value.

3. The method of claim 1, Wherein the primary fluid, first filled into the chamber (11), is controlled to have a temperature which is above the freezing point of the sample.

4. The method of claim 1, wherein the primary fluid comprises an alcohol.

5. The method of claim 1, wherein the primary fluid has a temperature which is below the freezing point of the sample (10);

and wherein the step of introducing the cryogenic fluid into the chamber is carried out immediately after the filling of the chamber with the primary fluid so that, before the pressure has reached said predetermined value, the sample (10) will not be cooled below the freezing point of the sample.

6. The method of claim 5, wherein the step of filling the sample chamber (11) with the primary fluid is carried out until the pressure has reached a second predetermined value which, optionally, is the same as said predetermined value.

7. The method of claim 5, wherein the temperature of the primary fluid is selected such that, as pressure rises in the sample chamber, the sample is effectively not heated.

8. The method of claim 1, wherein said primary fluid comprises a portion of said cryogenic fluid, and including the step of controlling the temperature of said portion of the cryogenic fluid by passing said portion through said heat exchanger (59) to be at a temperature which does not essentially heat the sample upon build-up of pressure within the chamber.

9. The method of claim 1, wherein said cryogenic fluid comprises liquid nitrogen, and said high pressure is at least 2,100 bar.

10. An apparatus for vitrifying of samples (10), particularly biological samples, said apparatus having structural means (13) forming a sample chamber (11);

a fluid outlet (35) leading from said sample chamber;

holder means (12, 33) to hold the sample within the chamber (11);

supply means (29, 57, 70) to supply said primary fluid to said chamber (11);

cryogenic fluid supply means (25, 36) to supply said highly pressurized cryogenic fluid to said chamber, and comprising, in accordance with the invention, means for establishing pressure within the chamber (11) while permitting escape of the primary fluid from the chamber and allowing the highly pressurized cryogenic fluid to flow into the chamber (11) to supercool the sample, said pressure establishing means including a controllable throttling or closing element (41) selectively at least essentially closing off said fluid outlet opening (35) from the chamber; and means (47, 49) for controlling opening of said throttling or closing element (41) selectively responsive to the pressure within the sample chamber (11) and permitting opening of said throttling or closing element only after the pressure within the chamber (11) has reached said predetermined value.

11. The apparatus of claim 10, further including valve means (34, 55) to stop supply of said primary fluid into the chamber (11) and cause introduction of the highly pressurized cryogenic fluid into the chamber (11).

12. The apparatus of claim 11, further including a control unit (32) controlling (a) the primary fluid supply means (57, 70) for filling the chamber (11) with primary fluid;

(b) introduction of highly pressurized cryogenic fluid into said chamber (11); and (c) operation of said throttling or closing element (41) to permit venting of said chamber (11) after the pressure within the chamber (11) has reached said predetermined value.

13. The apparatus of claim 12, further comprising a control element (73) coupled to said control unit and controlling an interlock system (63) interlocking sequential operation of said primary fluid supply means (29, 57, 70) and said cryogenic fluid supply means (25, 36) for controlling operation of said supply means until the pressure in the chamber, after having reached said predetermined value, has dropped to ambient pressure upon opening of said closing element (41).

14. The apparatus of claim 11, wherein the primary fluid comprises a portion of said highly pressurized cryogenic fluid; and wherein said valve means (55) controlling supply of said portion of cryogenic fluid to the chamber (11) at a pressure which is below the predetermined value of pressure at which said closing element (41) opens.

15. The apparatus of claim 14, further including a control unit (32) controlling (a) the primary fluid supply means (57, 70) for filling the chamber (11) with primary fluid;

(b) introduction of highly pressurized cryogenic fluid into said chamber; and (c) operation of said closing element (41) to permit venting of said chamber after the pressure within the chamber (11) has reached said predetermined value; and a function sensing means (71) coupled to said valve (55) and signaling to the control unit the open, or closed, position of said valve (55) controlling the supply of said primary fluid.

16. The apparatus of claim 11, further including an interlock means (64, 65, 67, 69) interlocking said closing element (41) and said valve means (55) to alternately connect said portion of the cryogenic fluid to the chamber and, after the sample chamber (11) has been filled with said portion, close said connection and open the connection to the cryogenic fluid supply means (25, 36).

17. The apparatus of claim 11, further including a bypass connection (57, 70) coupled to the cryogenic supply means (25, 36) for supplying a portion of highly pressurized cryogenic fluid to the chamber (11), said portion forming the primary fluid.

18. The apparatus of claim 17, further including a venting valve (38) coupled to the bypass (70) to permit venting the bypass after vitrification of a sample.

19. The apparatus of claim 17, wherein a valve forming of said valve means is connected between the bypass (57) and said sample chamber (11).

20. The apparatus of claim 17, wherein the bypass (70) forms a branch from the cryogenic supply means (25) to a valve (55) forming part of said valve means.

21. The apparatus of claim 17, further including a heat exchanger (59) connected in the flow path of the portion of the cryogenic fluid for selectively heating or cooling the cryogenic fluid being supplied as the primary fluid to said chamber.

22. The apparatus of claim 17, wherein said valve means comprises a pressure-sensitive valve (60) changing position when a preset pressure is reached.

23. The apparatus of claim 10, wherein said closing element comprises a spring-loaded valve (41, 47), and said pressure setting means comprises a spring (47), the spring tension of which is controllable.

24. The apparatus of claim 23, wherein said valve has an exchangeable valve seat element (37);

and a set of valve seat elements is provided, of respectively different through-put openings, for selective placement in the apparatus.

* * * * *